United States Patent
Suchan et al.

(10) Patent No.: US 8,651,334 B2
(45) Date of Patent: Feb. 18, 2014

(54) CARTRIDGE

(75) Inventors: Matthias Suchan, Hachenburg (DE); Alexander Bublewitz, Herborn (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 594 days.

(21) Appl. No.: 12/540,266

(22) Filed: Aug. 12, 2009

(65) Prior Publication Data
US 2010/0038381 A1     Feb. 18, 2010

(30) Foreign Application Priority Data
Aug. 14, 2008  (DE) .................. 10 2008 037 686

(51) Int. Cl.
*B67D 7/70*     (2010.01)
(52) U.S. Cl.
USPC .............. 222/137; 222/145.1; 222/145.6; 222/153.04; 222/326; 222/340; 222/341; 222/386
(58) Field of Classification Search
USPC ......... 222/136–137, 326–327, 340, 386, 129, 222/94, 153.04, 145.5, 330, 145.6, 145.1, 222/341; 604/191; 92/140
See application file for complete search history.

(56) References Cited

U.S. PATENT DOCUMENTS

| | | | | |
|---|---|---|---|---|
| 2,001,568 A * | 5/1935 | Creveling | ...................... | 222/257 |
| 2,748,991 A * | 6/1956 | McCarthy | ..................... | 222/387 |
| 3,033,424 A * | 5/1962 | Uno | ................ | 222/256 |
| 3,766,917 A | 10/1973 | Wimmer | | |
| 4,394,863 A * | 7/1983 | Bartner | ........................... | 604/90 |
| 4,431,414 A | 2/1984 | Lawrence | | |
| 4,583,934 A | 4/1986 | Hata et al. | | |
| 5,123,568 A * | 6/1992 | Keller | ............................ | 222/49 |
| 5,378,233 A * | 1/1995 | Haber et al. | .................... | 604/83 |
| 5,423,752 A * | 6/1995 | Haber et al. | .................... | 604/86 |
| 5,584,815 A * | 12/1996 | Pawelka et al. | ............... | 604/191 |
| 5,846,225 A * | 12/1998 | Rosengart et al. | ............. | 604/115 |
| 6,458,095 B1 * | 10/2002 | Wirt et al. | ....................... | 604/82 |
| 6,926,177 B1 | 8/2005 | Scott et al. | | |
| 7,748,980 B2 * | 7/2010 | Mulhauser et al. | ............. | 433/89 |
| 7,815,598 B2 * | 10/2010 | Hommann et al. | ............. | 604/89 |

FOREIGN PATENT DOCUMENTS

| | | |
|---|---|---|
| DE | 3428202 A1 | 2/1985 |
| DE | 60111210 T2 | 2/2006 |
| DE | 102006017209 A1 | 10/2007 |
| DE | 202008007801 U1 | 9/2008 |
| EP | 0378434 A2 | 7/1990 |
| EP | 0624403 B1 | 8/1997 |
| EP | 1256389 A2 | 11/2002 |
| EP | 1679126 A1 | 7/2006 |
| WO | 9600524 A1 | 1/1996 |
| WO | 2009/036962 A2 | 3/2009 |

* cited by examiner

*Primary Examiner* — Frederick C Nicolas
(74) *Attorney, Agent, or Firm* — McDonnell Boehnen Hulbert & Berghoff LLP

(57) ABSTRACT

The invention pertains to a cartridge (1) with at least one chamber (6a, 6b) for accommodating a substance that respectively features a dispensing opening (11a, 11b) and another opening that is closed by a piston (8a, 8b) that can be displaced in the chamber and serves for dispensing the substance. The cartridge (1) furthermore features a piston rod mechanism (4) for displacing the piston (8a, 8b) in the chamber (6a, 6b). In this case, the piston rod mechanism is composed of several piston rods (14, 14a, 14b, 15, 15') that can be transferred from a first dispensing stage to a second dispensing stage with the aid of a spring element (18, 18a, 18b).

18 Claims, 5 Drawing Sheets

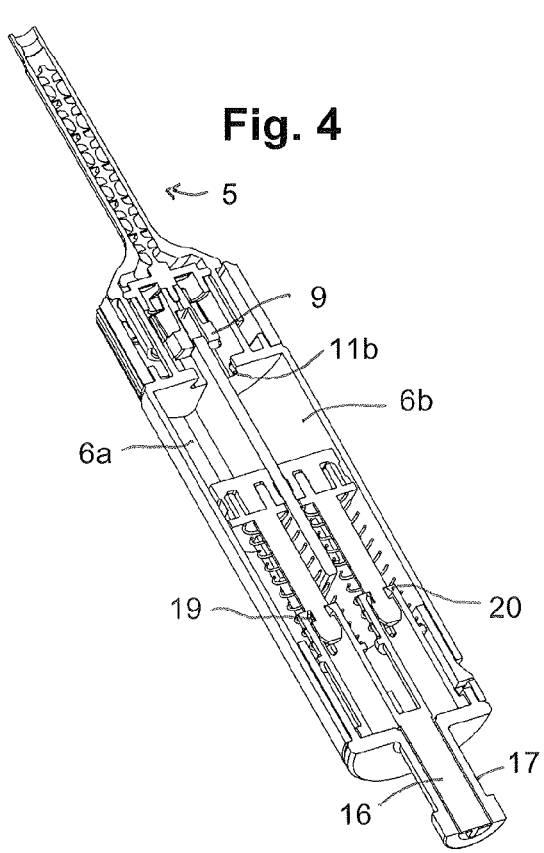
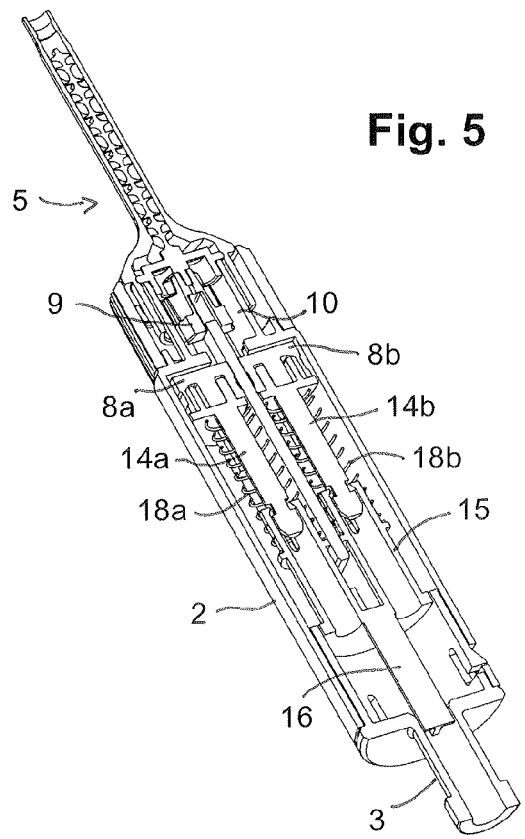
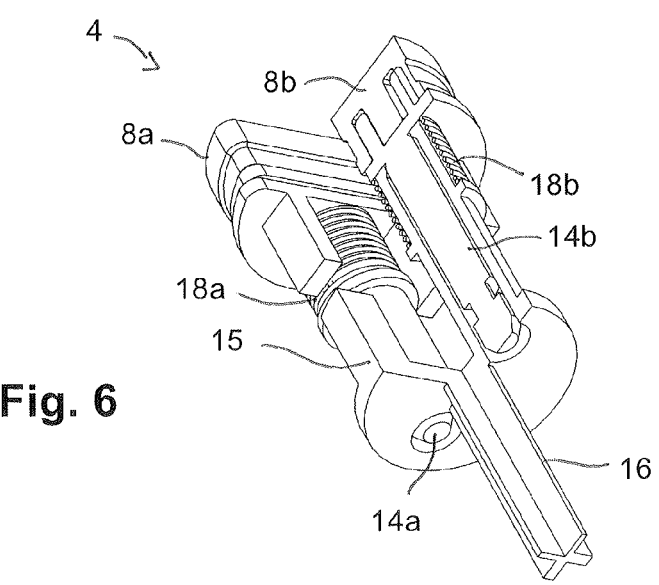

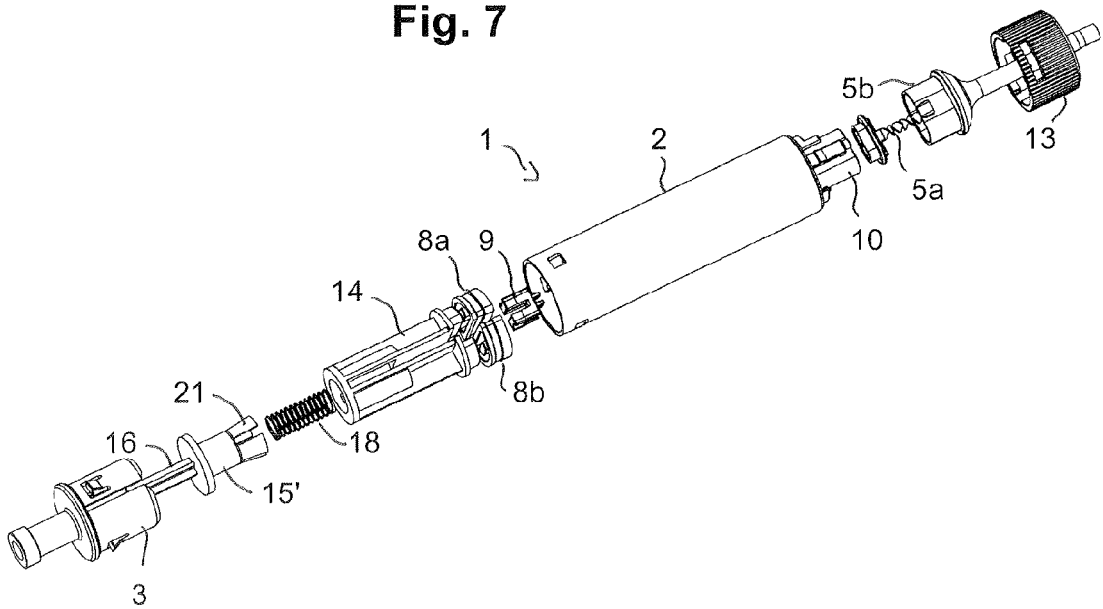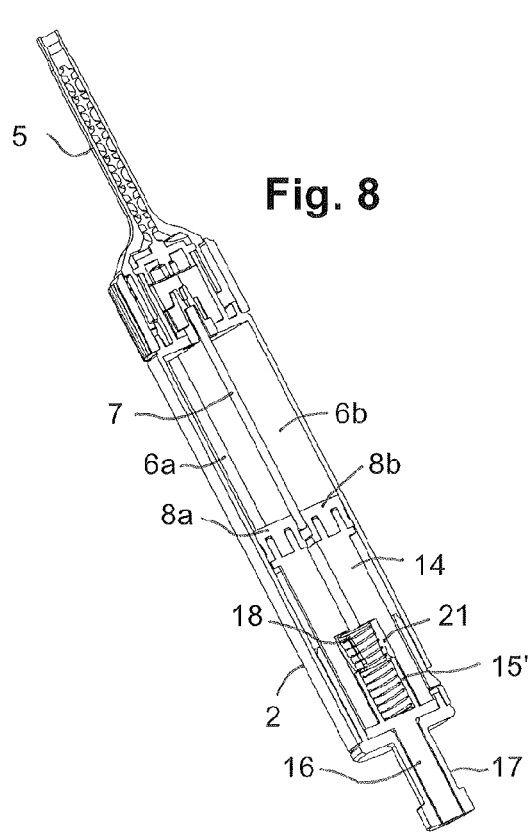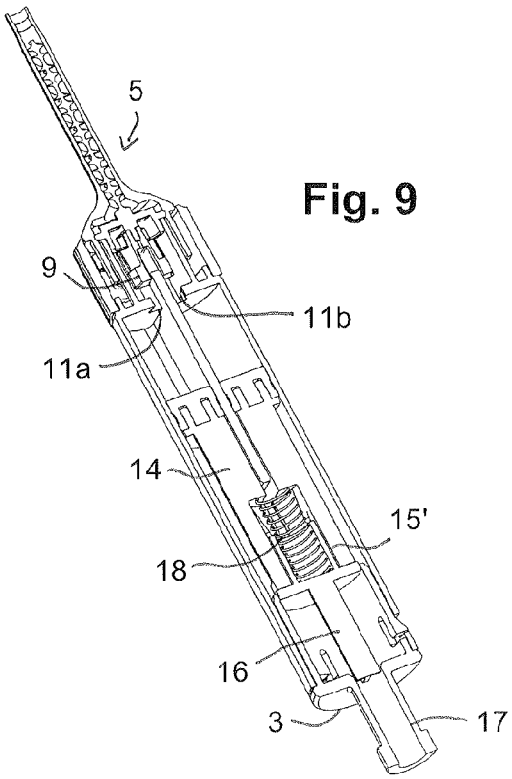

CARTRIDGE

CROSS-REFERENCE TO RELATED APPLICATIONS

This application claims priority under 35 U.S.C. §119(a)-(d) to German patent applications no. 10 2008 037.686.8, filed Aug. 14, 2008, which is hereby incorporated by reference in its entirety.

BACKGROUND OF THE INVENTION

1. Field of the Invention

The invention relates generally to a cartridge that can be used, for example, to dispense single- or multi-component substances such as dental materials. The invention relates more particularly to a cartridge with at least one chamber for accommodating a substance that respectively features a dispensing opening and another opening that is closed by a piston that can be displaced in the chamber and serves for dispensing the substance, and with a piston rod mechanism for displacing the piston in the chamber.

2. Technical Background

Cartridges as described above are known for various applications, e.g., for storing and dispensing single-component or multi-component material immediately before it is processed, particularly in the field of dentistry. EP 1 679 126 A1 and EP 0 624 403 B1 respectively disclose cartridges for storing and dispensing two components, wherein a piston rod is provided that protrudes from the rear side of the cartridge.

Furthermore, TAH Industries Inc. of Robbinsville, USA, offers a cartridge of the above-mentioned type with two chambers that are arranged coaxial to and essentially behind one another and can be emptied by means of a pot-like transfer piston under the designation "u-TAH™ nano." This cartridge is delivered with a sealing cap that needs to be removed prior to the initial use of the cartridge in order to attach, if applicable, a separate mixer or similar applicator to the cartridge. The cartridge "u-TAH™ nano" features a holding section suitable for being connected to a dispensing gun that is sold, e.g., under the designation "Centrix®" by Centrix Inc. of Shelton, USA. Such a gun is also illustrated in EP 1 256 389 A2.

This dispensing gun features a plunger that can be pushed forward into the cover of the cartridge by a defined distance such that the piston arrangement is pushed forward within the chamber in order to dispense the substances accommodated in the chambers. One peculiarity of these known cartridges can be seen in that they can be completely emptied with only one stroke of the plunger of the dispensing gun. Consequently, the plunger of the dispensing gun can be moved forward and backward by no more than the defined amount.

This type of cartridge can accommodate and dispense relatively large quantities of the substances, because the cross section of the chambers is increased for a given stroke of the plunger of the dispensing gun such that a larger quantity of the substances can be dispensed with each stroke of the plunger. However, this is perceived disadvantageous not only for optical reasons, but also because an exact metering is very difficult because a large quantity of the substance is already dispensed from the cartridge with a small stroke of the plunger. Furthermore, the force that is required for dispensing the substances and increases proportionally with the cross section, as well as the confined space conditions, for example, in the oral cavity, make it more difficult to utilize cartridges with a large cross section.

There remains a need in the art for cartridges that can accommodate and dispense larger quantities of the substances without suffering these disadvantages.

SUMMARY OF THE INVENTION

One aspect of the invention is a cartridge comprising at least one chamber for accommodating a substance, the chamber comprising a dispensing opening and a second opening; a piston that closes the second opening and can be displaced in the chamber and serves for dispensing the substance; and a piston rod mechanism for displacing the piston in the chamber, wherein the piston rod mechanism features at least one first piston rod that faces the piston, at least one second piston rod interconnectable with the first piston rod (for example, by a means for connecting the first piston rod with the second piston rod), and at least one spring element that is pretensioned between the first piston rod and the second piston rod, and wherein the piston rods can be transferred from a first dispensing stage, in which the first piston rod is at least sectionally arranged adjacent to the second piston rod, to a second dispensing stage, in which the first and second piston rods are arranged essentially behind one another and interconnected.

In a cartridge according to one embodiment of the invention, the piston rod mechanism features at least a first piston rod that faces the piston and at least one second piston rod interconnectable with the first piston rod. The first and second piston rods can be interconnectable, for example, in a positive (i.e., form fit) fashion, or a non-positive (i.e., force-fit) fashion. The piston rod mechanism includes at least one spring element that is pretensioned between the first piston rod and the second rod piston rod. In this case, the piston rods can be transferred from a first dispensing stage, in which the first piston rod is at least sectionally or partially arranged adjacent to the second piston rod, to a second dispensing stage, in which the first and the second piston rod are essentially arranged behind one another and interconnected by a spring element. The cartridge makes it possible to respectively dispense a quantity of the substance from the chamber successively in two (or more) stages. This requires two successive strokes of the plunger of the dispensing gun.

The connection of the piston rods in the second dispensing stage is preferably provided by of a snap-on or snap-in connection. It would also be possible to alternatively or additionally provide, for example, a clamping connection.

A particularly exact metering can be realized because only a small quantity of the substance is dispensed with each stroke of the plunger. Furthermore, the cartridge may have a preferably cylindrical elongate shape that is also preferred for optical reasons. In this case, the piston rod mechanism can be realized in such a way that both piston rods initially carry out a first stroke jointly and the spring element between the two piston rods remains tensioned during this first dispensing stage, and that the first piston rod and the second piston rod are initially moved relative to one another due to the force of the spring element and subsequently interconnected, preferably by means of a snap-on connection, during a retraction of the plunger of the dispensing gun in the second dispensing stage, namely such that both piston rods can then once again be pushed forward jointly during a second stroke. Since the two piston rods are essentially arranged adjacent to one another in the first dispensing stage and behind one another in the second dispensing stage, the length of the piston rod mechanism changes between the first dispensing stage and the second dispensing stage.

The connection between the piston rods in the second (or additional) dispensing stage may be realized such that the first stroke needs to be executed in its entirety before the piston rods can be interconnected. Alternatively, the piston rods may also be interconnected irrespective of the fact whether the first stroke was executed in its entirety, i.e., irrespective of the fact whether the first piston rod was initially pushed forward to its maximum, particularly if the piston rods are interconnected by means of a clamping connection or, for example, a snap-in connection with a plurality of teeth.

In the first dispensing stage, the at least two piston rods of the piston rod mechanism do not have to be arranged entirely adjacent to one another; for example, it can suffice if they sectionally overlap in the axial direction, i.e., in the forward direction, during the dispensing process. Furthermore, the first piston rod and the second piston rod also do not have to be arranged exactly behind one another in the second dispensing stage, but rather may also sectionally overlap and, in particular, do not have to be arranged in alignment with one another as long as the length of the piston rod mechanism is increased in comparison with the first dispensing stage. However, it is particularly preferred that the first piston rod and the second piston rod are telescopically arranged in one another during the first dispensing stage. To this end, one of the piston rods may be provided with a bore or a similar opening, in which the other piston rod is guided. The piston rods may also be realized in a sleeve-like fashion, wherein these sleeves are telescopically pushed into one another during the first dispensing stage and pulled apart during the second dispensing stage.

In order to interconnect the piston rods in such a way during the second dispensing stage that they can be jointly pushed forward, a snap-in groove may be provided in one of the piston rods and a snap-in tab that engages with the snap-in groove may be provided on the other piston rod. Alternatively or additionally, at least one expansion or snap-in web may be provided on at least one of the piston rods such that it snaps from a position during the first dispensing stage, in which the piston rods can be displaced relative to one another, into a second position during the second dispensing stage, in which a displacement of the piston rods relative to one another is blocked in at least one direction, namely in dependence on the relative position between the piston rods. According to one embodiment of the invention, it is particularly preferred that the snap-in connection between the piston rods engages automatically as soon as the spring element has moved the two piston rods sufficiently far relative to one another. However, it would basically also be possible to lock the piston rods in the extended position of the piston rod mechanism, e.g., by means of a manual engagement.

In order to improve the metering accuracy when the at least one substance is dispensed from the cartridge, it is preferred that the second piston rod is directly supported on the first piston rod during the first and the second dispensing stage. The force for pushing the at least one piston forward in the chamber is not transmitted by the spring element, e.g., a pressure spring, but the piston rods are rather directly supported on one another. Alternatively, at least one preferably rigid intermediate element that serves for transmitting the dispensing force may be provided between the piston rods.

The cartridge according to certain embodiments of the present invention is not only suitable for storing and for dispensing a single substance in/from a single chamber, but can also be suitable for separately storing and jointly dispensing several substances in/from different chambers. The design of the chambers and the cartridge may be realized, in particular, as described in DE 20 2008 007 801 U, which is hereby incorporated herein by reference in its entirety.

If several chambers are arranged behind and/or adjacent to one another in the cartridge, a piston and a piston rod or at least a section of a piston rod can be respectively assigned to each chamber. According to one particularly preferred embodiment of the invention, two chambers that respectively have an approximately semicircular cross section are arranged adjacent to one another in the cartridge such that the cartridge essentially has an altogether cylindrical outer contour. According to another preferred embodiment of the invention, two chambers that concentrically encompass one another are provided, wherein the outer chamber defines an annular space that surrounds the inner chamber. In this case, the pistons may be realized in the form of an annular piston for the outer chamber and, e.g., a circular piston for the inner chamber. It would furthermore be possible to arrange the two chambers behind one another, wherein a preferably central outlet channel for the rear chamber extends through the front chamber. In this case, the front end represents the distal end, i.e., the end on which the at least one dispensing opening is provided, while the end that is closed by the at least one piston represents the proximal or rear end.

In order to utilize the cartridge of the present invention in a dispensing gun such as, e.g., the above-described "Centrix®" dispensing gun, it is preferred that the piston rod mechanism also features a transfer piston that is guided in a displaceable fashion in the end situated opposite of the at least one dispensing opening. In this case, the transfer piston is guided in a cylindrical section with a thickened end of the cover, wherein the transfer piston preferably ends essentially flush with the end of the cylindrical section of the cover in the initial state. Consequently, the plunger of the dispensing gun penetrates into this cylindrical section of the cover in order to dispense the at least one substance from the cartridge and simultaneously pushes the transfer piston toward the at least one dispensing opening such that the piston rods are also pushed forward. The transfer piston and the at least one piston rod are preferably realized in one piece. Alternatively, the transfer piston may also be realized in the form of a separate component.

On its distal end that features the at least one dispensing opening, the cartridge may feature an applicator that may be realized, e.g., in the form of a dispensing tube and/or a mixer. In this case, it is preferred that the applicator already is rigidly connected to the cartridge in the filled initial state of the cartridge such that the applicator does not have to be mounted and preferably also not activated prior to the initial use of the cartridge. The user-friendliness of the cartridge can be significantly improved if it is merely required to insert the cartridge into a dispensing gun and to subsequently actuate this gun, i.e., if no other steps are necessary. Such an intuitive utilization of the cartridge can also reduce the risk of operating errors. In this case, the applicator may either be inseparably connected to the cartridge or realized in an exchangeable fashion such that the at least one substance accommodated in the cartridge can be dispensed during several successive applications.

In order to maintain the at least one substance accommodated in the cartridge largely germ-free during the transport and the storage and to prevent the admission of dirt, as well as a discharge of the at least one substance, the cartridge can be sealed by the at least one piston on the proximal side, but also on the distal side. To this end, it is preferred that the at least one dispensing opening is sealed with a sealing mechanism prior to the initial dispensation of a substance from the cartridge. It is also preferred that this sealing mechanism is opened automatically, i.e., preferably during the intuitive utilization of the cartridge. This can preferably be realized in such a way that the internal pressure of the substance in the chamber displaces the sealing mechanism within the dispensing channel in such a way that a flow connection between the chamber and, e.g., the applicator or the dispensing opening is released. Alternatively or additionally, it would also be possible that the sealing mechanism cooperates with the applicator, wherein the sealing mechanism can be opened by displacing the applicator or another component relative to the cartridge. This displacement may consist of an axial movement, a radial movement and/or a rotational movement. We also refer to DE 20 2008 007 801 U with respect to the sealing mechanism and the opening of the cartridge.

According to one embodiment of the invention, the force of the at least one spring element is adapted to the sealing mechanism in such a way that the sealing mechanism cannot be opened by the force of the spring element alone. This ensures that the piston rods of the piston rod mechanism are not already displaced relative to one another during the transport or the storage in such a way that the internal pressure within the at least one chamber increases to a level that suffices for automatically opening the sealing mechanism. To this end, it is preferred that the piston rods can be displaced relative to one another in a particularly smooth-running fashion such that the spring element only needs to exert a low force in order to transfer the piston rod mechanism from the first dispensing stage to the second dispensing stage.

Alternatively or additionally, it would be possible to separably lock the piston rods in a position, in which the spring element is compressed, during the first dispensing stage, i.e., at least before the first piston rod is initially pushed forward. The locked piston rods can be separated, e.g., automatically by pushing the piston rod mechanism forward during the first dispensing stage. This precludes any influence of the spring element on the sealing mechanism during the transport and the storage of the cartridge.

Another aspect of the invention is a piston rod mechanism that can be used, for example, in a cartridge of the above-described type. According to the invention, this piston rod mechanism features a first piston rod and a second piston rod that are essentially arranged adjacent to one another in a first compressed state and can be transferred to a second expanded state, in which the piston rods are essentially arranged behind one another. In the second state, lock mechanism provided on at least one of the piston rods blocks a return to the first state. The optionally separable lock mechanism may consist of mutually assigned snap-in grooves and snap-in tabs and/or snap-in webs. The transfer from the first to the second state is preferably realized automatically, for example, with a pressure spring.

DESCRIPTION OF THE DRAWINGS

The invention will be described in more detail below with the aid of examples of embodiment and with reference to the drawing. Schematically:

FIG. 4 is a sectional view through the cartridge according to FIG. 1 during the second dispensing stage;

FIG. 5 is a sectional view through the cartridge according to FIG. 1 in the emptied state;

FIG. 6 is a partially sectioned perspective representation of the piston rod mechanism of the cartridge according to FIG. 1;

FIG. 7 is an exploded view of a cartridge according to a second embodiment of the invention;

FIG. 8 is a sectional view through the cartridge according to FIG. 7 prior to the initial use;

FIG. 9 is a sectional view through the cartridge according to FIG. 7 after the end of the first dispensing stage;

DETAILED DESCRIPTION

Figure 1:
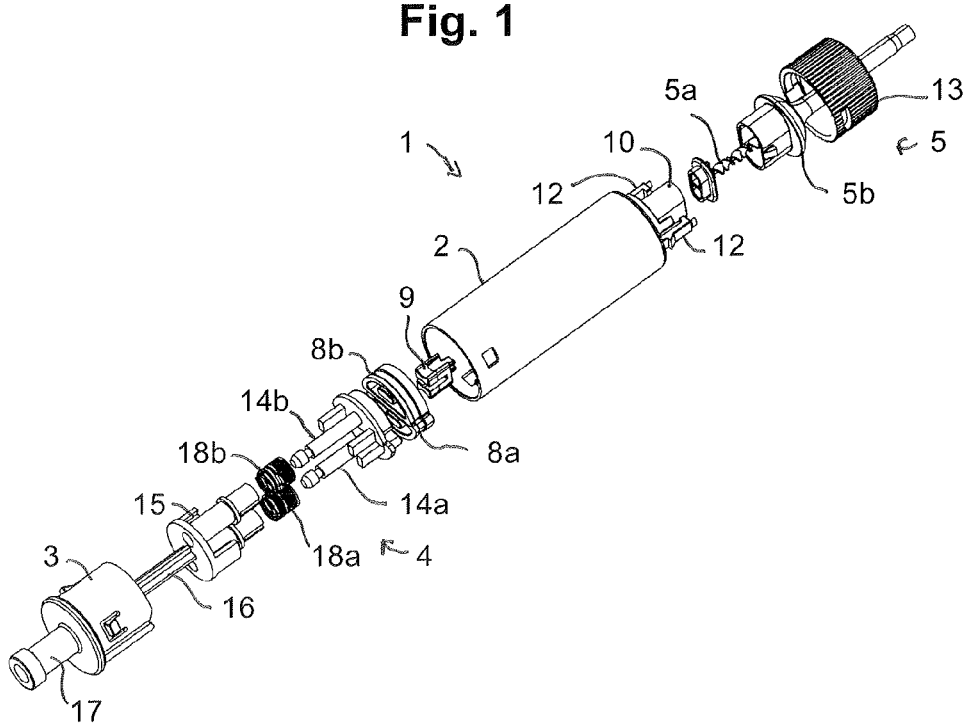
FIG. 1 is an exploded view of a cartridge according to a first embodiment of the invention.

The cartridge 1 illustrated in FIGS. 1 to 6 is essentially composed of a cylindrical housing 2, a cover 3, a piston rod mechanism 4 that can be displaced therein and an applicator 5 that is realized in the form of a mixer in the embodiment shown.

Two chambers 6a and 6b of approximately semicircular cross section are defined by a partition wall 7 and the housing 2 and arranged adjacent to one another in the housing 2. On the rear end of the housing 2 that carries the cover 3, the chambers 6a and 6b are respectively closed by a piston 8a and 8b that can be displaced within the chambers in a sealing fashion. The opposite end of the chambers is closed by a sealing piston 9 that can be displaced in the dispensing direction in a dispensing channel for the substances accommodated in the chambers. In the position of the sealing piston 9 illustrated in FIG. 2, this sealing piston seals the respective dispensing openings 11a and 11b in the chambers 6a and 6b. In contrast to the illustration in FIG. 1, the sealing piston 9 is inserted into the housing from the side that faces the applicator 5.

The applicator 5 is realized in the form of a static mixer that features a mixer helix 5a and a mixer sleeve 5b. In the embodiment shown, the mixer helix 5a can be inserted into the dispensing channel 10 while the mixer sleeve 5b surrounds the dispensing channel 10 with its distal end. In order to fix the mixer 5 on the housing 2, a coupling arrangement for separably attaching the mixer or any other applicator is provided. In the embodiment shown, the coupling arrangement features two spring arms 12 that are arranged on the front side of the housing 2 adjacent to the dispensing channel 10. Hooks provided on the spring arms 12 are directed radially inward and can engage behind corresponding snap-in tabs on the distal apron of the mixer sleeve 5b when the spring arms 12 are placed against the distal apron of the mixer sleeve 5b due to a rotation of the locking ring 13. If the locking ring 13 that is held on the housing in an axially rigid yet rotatable fashion is turned in the opposite direction, the spring arms 12 are spread apart in order to release the mixer 5 from the housing 2.

The enlarged illustration according to FIG. 6 also shows that the piston rod mechanism 4 features a two-part first piston 14a, 14b that is connected to the pistons 8a, 8b. A free space is formed between the two first piston rods 14a, 14b such that the first piston rod can be pushed over the partition wall 7. A second piston rod 15 and a transfer piston 16 that is guided in a displaceable fashion in a cylindrical section 17 of the cover 3 are realized in one piece. A pressure spring 18a and 18b is respectively provided between the two parts 14a and 14b of the first piston rod and the second piston rod 15, wherein said pressure spring is illustrated in its compressed state in FIG. 2. The second piston rod 15 is also provided with a slot or free space for the partition wall 7.

The first piston rod essentially consists of two pin-shaped elements 14a and 14b that extend toward the cover 3 while the second piston rod 15 features two sleeve-like sections, in which the pin-like elements 14a, 14b of the first piston rod are guided in a displaceable fashion. In the telescoped position of the pin-like elements and the sleeve-like sections illustrated in FIGS. 2 and 6, a front wall of the sleeve-like sections abuts a widened top surface of the two parts of the first piston rod. The respective pressure springs 18a and 18b are arranged such that they surround the sleeve-like sections of the second piston rod 15 in this case. The pin-like elements 14a, 14b of the first piston rod are respectively provided with a snap-in groove 19 on their proximal end. On the inner side of their front distal end, the sleeve-like sections of the second piston rod 15 are provided with snap-in tabs 20.

Figure 2:
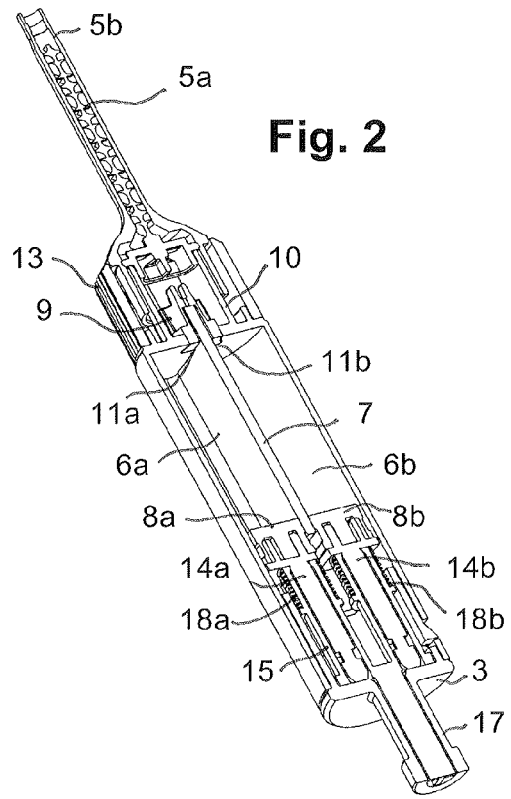
FIG. 2 is a sectional view through the cartridge according to FIG. 1 prior to the initial use.
Figure 3:
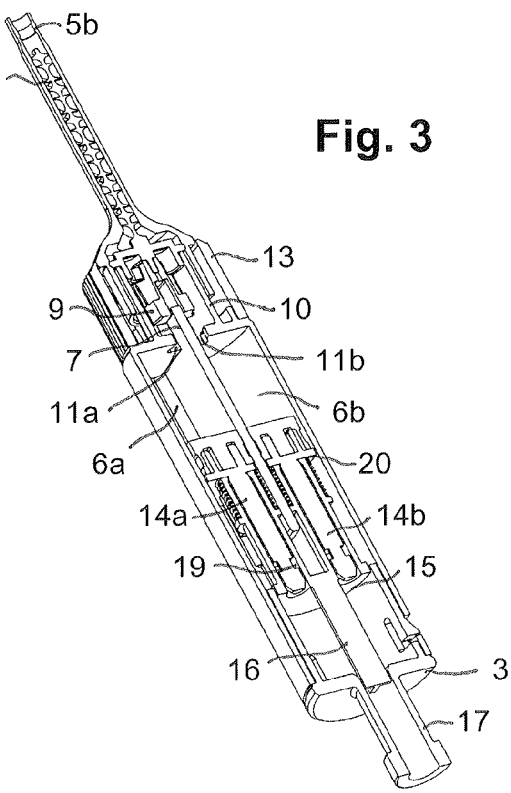
FIG. 3 is a sectional view through the cartridge according to FIG. 1 after the end of the first dispensing stage.

In the initial state of the cartridge 1 illustrated in FIG. 2, both chambers 6a and 6b are respectively filled with a not-shown substance. The two piston rods are telescopically pushed into one another such that the piston rod mechanism 4 is comparatively short in the axial direction, i.e., in the dispensing direction. In this case, the transfer piston 16 ends essentially flush with the cylindrical section 17 of the cover 3. The substances are dispensed from the chambers 6a and 6b in two successive stages. During the first dispensing stage, a plunger that is not illustrated in the figures is pushed into the cylindrical section 17 of the cover 3 such that the transfer piston 16 is pushed forward in the dispensing direction. This also causes the second piston rod 15 and the first piston rod 14, on which the sleeve-like sections of the second piston rod 15 are supported, to be pushed forward together with the pistons 8a and 8b such that the pressure in the chambers 6a and 6b increases. Consequently, the sealing piston 9 that seals the dispensing openings 11a, 11b of the chambers is pushed forward in the dispensing channel 10 such that the substances can flow from the chambers 6a and 6b through the dispensing openings and into the dispensing channel around the sealing piston 9 and ultimately into the applicator 5. In this respect, FIG. 3 shows the end of the first dispensing stage, at which the piston rod mechanism is pushed forward into the chambers to such a degree that approximately one-half of the substances is dispensed. The transfer piston 16 is almost completely pushed out of the cylindrical section 17 in this case.

When the plunger of the dispensing gun now once again returns into its original position, the force of the two pressure springs 18a, 18b causes the second piston rod 15 to be pushed rearward relative to the two parts 14a, 14b of the first piston rod together with the transfer piston 16, namely until the piston rod mechanism assumes the extended position shown in FIG. 4. In this case, the transfer piston once again ends essentially flush with the end of the cylindrical section 17. The position of the snap-in tabs 20 and the snap-in grooves 19 is chosen in such a way that the snap-in tabs 20 can engage into the snap-in grooves 19 in the position illustrated in FIG. 4 and the piston rods 14 and 15 are rigidly interconnected in the axial direction.

In a second dispensing stage, the plunger of the dispensing gun can be once again displaced into the cylindrical section 17 of the cover 3 such that the transfer piston 16 is once again pushed forward in the dispensing direction. The two piston rods are jointly pushed forward in the chambers as shown in FIG. 5 due to the fact that the two piston rods are interlocked by means of the snap-in tabs 20 and the snap-in grooves 19. This makes it possible to completely empty the chambers 6a, 6b of the cartridge 1 with two successive actuations of the plunger on the dispensing gun.

A similar embodiment is illustrated in FIGS. 7-12, wherein the structure of the housing 2, the cover 3, the applicator 5, the coupling arrangement and the sealing piston 9 corresponds to that of the first embodiment.

The piston rod mechanism according to the second embodiment features a first piston rod that carries the two pistons 8a and 8b to be displaced in the chambers 6a and 6b. In this case, the first piston rod 14 is at least sectionally realized in the form of a slotted sleeve, wherein the slot in the sleeve has such dimensions that the first piston rod 14 can be pushed over the partition wall 7. The second piston rod 15' and the transfer piston 16 are once again realized in one piece, wherein the second piston rod also has an approximately sleeve-like shape such that the second piston rod 15' can be displaced in the first piston rod 14. A pressure spring 18 is accommodated between the first piston rod 14 and the second piston rod 15' and guided in the sleeve-shaped section of the second piston rod 15'.

Furthermore, several snap-in webs 21 are provided on the front end of the second piston rod 15' referred to the forward direction, i.e., the distal end thereof, and spread outward referred to the sleeve-like section of the second piston rod 15' in their unstressed state. However, the snap-in webs 21 can be pressed radially inward against elastic restoring forces such that an outside diameter described by the snap-in webs 21 approximately corresponds to that of the sleeve-like section of the second piston rod 15'. This means that the piston rod 15' can be inserted into the cylindrical recess in the first piston rod 14 together with the snap-in webs 21.

Figure 10:
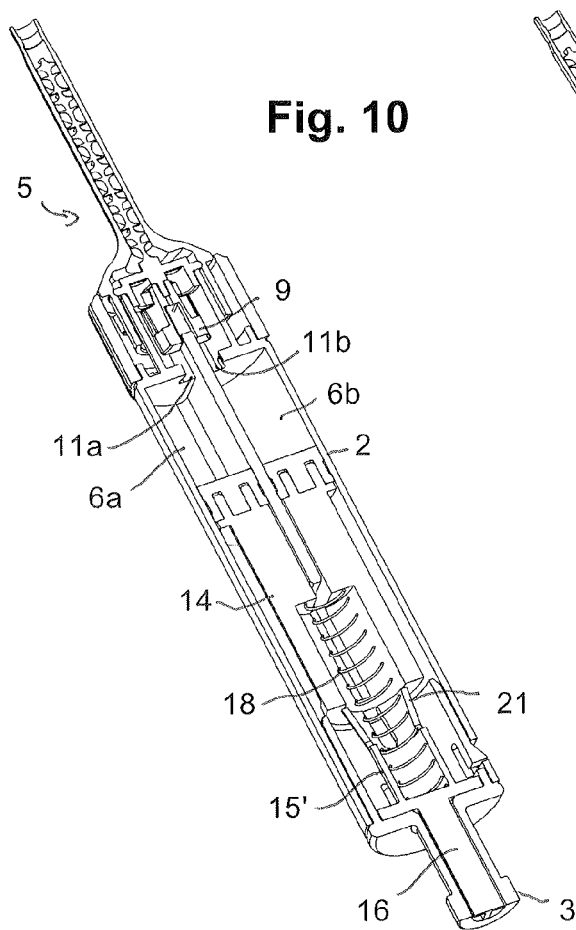
FIG. 10 is a sectional view through the cartridge according to FIG. 7 during the second dispensing stage.
Figure 11:
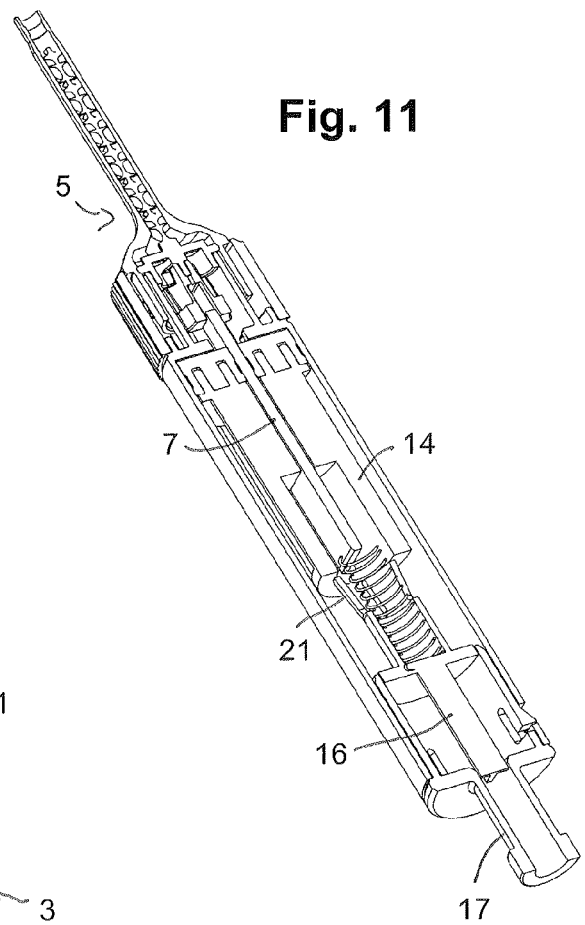
FIG. 11 is a sectional view through the cartridge according to FIG. 7 in the emptied state.
Figure 12A:
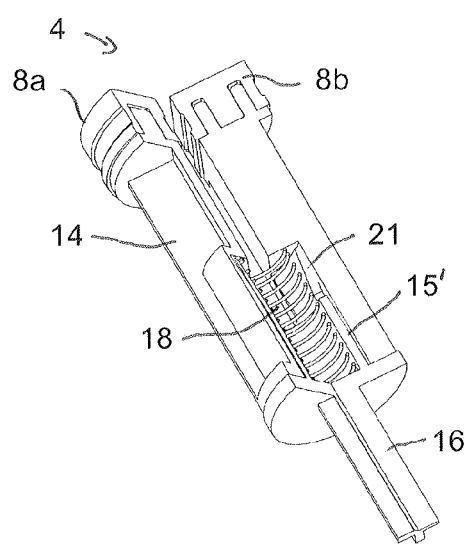
FIGS. 12a and 12b are partially sectioned perspective representations of the piston rod mechanism of the cartridge according to FIG. 7.
Figure 12B:
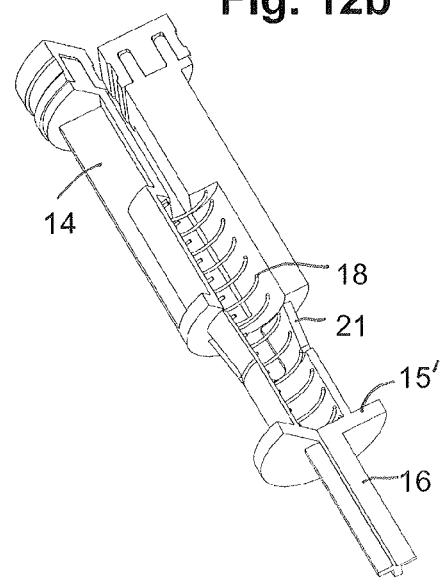

The dispensing of substances from the cartridge in accordance with the second embodiment essentially takes place as described above with reference to the first embodiment. The two piston rods 14 and 15' initially are telescopically pushed into one another as shown in FIGS. 8 and 12a. FIG. 9 shows the end of the first dispensing stage, at which approximately one-half of the substances is dispensed from the two chambers. The two piston rods 14 and 15' are telescopically extended relative to one another after the retraction of the plunger of the dispensing gun or the like. As soon as the distal front sides of the snap-in webs pass the proximal front surface of the first piston rod 14, the snap-in webs 21 spread radially outward as shown in FIGS. 10 and 12b.

If a plunger is now once again pushed into the cylindrical section 17 of the cover 3 during the second dispensing stage, the second piston rod 15' is supported on the proximal end of the first piston rod 14 by means of the snap-in webs 21 such that both piston rods can once again be jointly pushed forward in the housing 2. According to FIG. 11, the pressure spring 18 is once again partially compressed by the partition wall 7 during this process. Consequently, the second piston rod 15' can be once again partially pushed back in the housing 2 after the end of the second dispensing stage.

Figure 13:
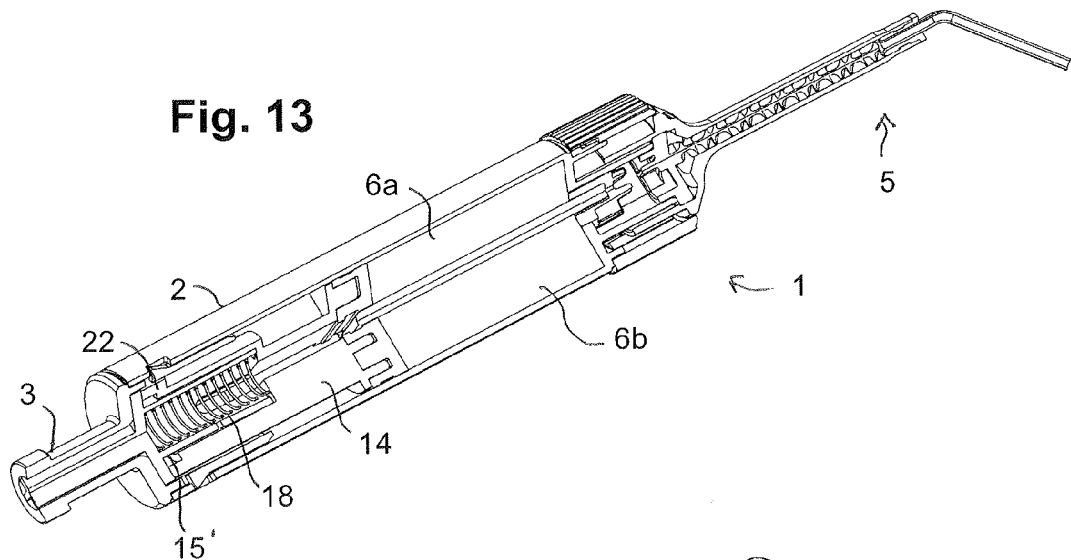
FIG. 13 is a sectional view through a cartridge according to another embodiment prior to the initial use.
Figure 14A:
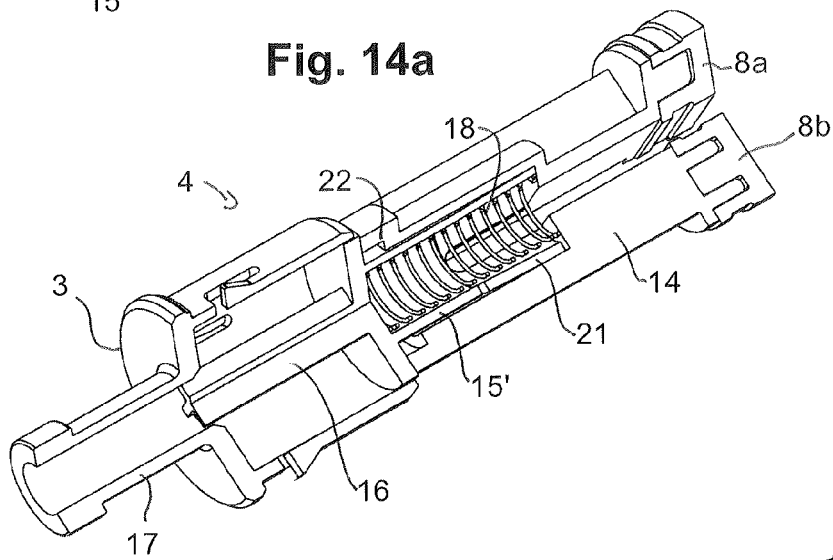
FIGS. 14a and 14b are partially sectioned perspective representations of the piston rod mechanism of the cartridge according to FIG. 13.
Figure 14B:
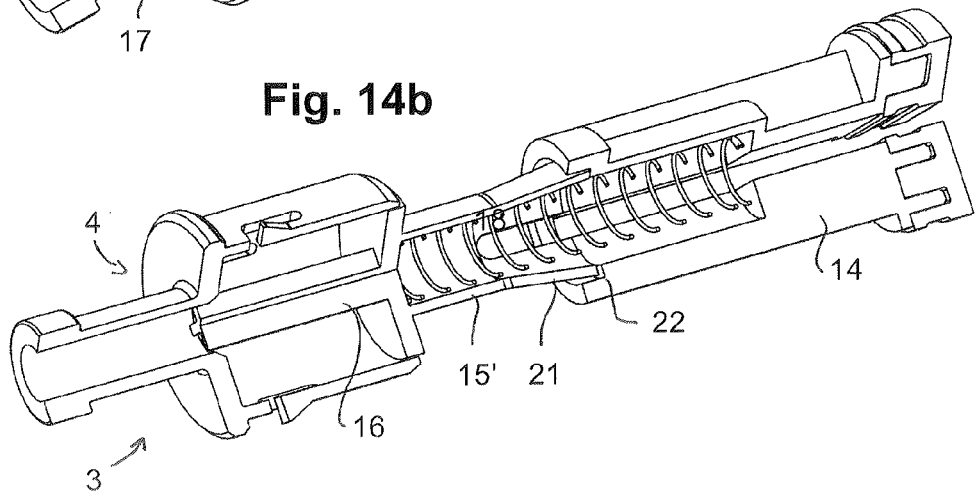

FIGS. 13, 14a and 14b show a variation of the above-described embodiment, in which a cylindrically widened support surface 22 is provided in the first piston rod 14 on its proximal end, wherein the snap-in webs 21 of the second piston rod 15' are supported on this widened support surface during the second dispensing stage.

It is possible to realize arrangements and designs of the chambers 6a, 6b that differ from the embodiments shown.

Furthermore, would also be possible to provide only a single chamber or additional chambers. In the two embodiments illustrated in the figures, the piston rod mechanism 4 is designed in such a way that the cartridge can be emptied in two dispensing stages. However, a corresponding modification of the piston rod mechanism 4 would also make it possible to realize additional dispensing stages such that even larger quantities of the substances can be dispensed. It would also be possible to realize the mounting and the design of the mixer 5 (applicator) different from the embodiment illustrated in the figures.

In the embodiments shown, a positive snap-in or snap-on connection is provided between the piston rods. Additionally or alternatively to such a snap-type connection, the piston rods could also be fixed relative to one another in their extended state by means of wedging or pressing. It would even be conceivable that a projection or an edge of one of the piston rods digs into the material of the other piston rod. A person skilled in the art basically may provide any suitable positive or non-positive connection.

The invention claimed is:

1. A cartridge comprising at least one chamber for accommodating a substance, the chamber comprising a dispensing opening and a second opening;
   a piston that closes the second opening and can be displaced in the chamber and serves for dispensing the substance; and
   a piston rod mechanism for displacing the piston in the chamber,
   wherein the piston rod mechanism comprises at least one first piston rod that faces the piston, at least one second piston rod interconnectable with the first piston rod, and at least one spring element that is pretensioned between the first piston rod and the second piston rod, and
   wherein the piston rods can be transferred from a first dispensing stage, in which the first piston rod is at least sectionally arranged adjacent to the second piston rod, to a second dispensing stage, in which the first and second piston rods are arranged essentially behind one another and interconnected.

2. The cartridge according to claim 1, wherein the first piston rod and the second piston rod are telescopically arranged in one another in the first dispensing stage.

3. The cartridge according to claim 1, wherein a snap-in groove is provided in one of the piston rods and a snap-in tab for engaging with the snap-in groove is provided in the other piston rod.

4. The cartridge according to claim 1, wherein at least one expansion or snap-in web is provided on at least one of the piston rods and snaps from a position, in which the piston rods can be displaced relative to one another during the first dispensing stage, to a second position, in which a displacement of the piston rods relative to one another is blocked in at least one direction during the second dispensing stage, namely in dependence on the relative position between the piston rods.

5. The cartridge according to claim 1, wherein the second piston rod is directly supported on the first piston rod during the first and the second dispensing stage.

6. The cartridge according to claim 1, wherein the cartridge comprises several chambers that are arranged behind and/or adjacent to one another and to which a piston and a piston rod or a piston rod section are respectively assigned.

7. The cartridge according to claim 1, wherein the piston rod mechanism also features a transfer piston that is guided in a displaceable fashion in a cover that is situated opposite of the at least one dispensing opening.

8. The cartridge according to claim 1, wherein an applicator is fixed on the end of the cartridge that features the at least one dispensing opening.

9. The cartridge according to claim 1, wherein the at least one dispensing opening is sealed by a sealing mechanism that can be opened automatically.

10. The cartridge according to claim 9, wherein the force of the at least one spring element is adapted to the sealing mechanism in such a way that the sealing mechanism cannot be opened by the force of the spring element alone.

11. The cartridge according to claim 1, wherein the piston rods are separably locked in a position, in which the spring element is compressed during the first dispensing stage, namely at least prior to the initial displacement of the first piston rod.

12. The cartridge according to claim 1, wherein the chamber contains a dental material.

13. A piston rod mechanism according to claim 8, wherein the applicator is fixed in a separable fashion on the end of the cartridge.

14. A piston rod mechanism according to claim 9 wherein the sealing mechanism is opened automatically by an internal pressure in the at least one chamber.

15. A piston rod mechanism according to claim 9 wherein the sealing mechanism is opened automatically by displacing an applicator prior to the initial dispensation of a substance from the cartridge.

16. A piston rod mechanism comprising
    a first pin-shaped piston rod and a second sleeve-like piston rod that are essentially arranged telescopically to one another in a first compressed state, wherein the first pin-shaped piston rod resides within the second sleeve-like piston rod, and
    that can be automatically transferred to a second expanded state, in which the first pin-shaped piston rod is guided out of the second sleeve-like piston rod in a displaceable fashion such that the first and second piston rods are essentially arranged behind one another,
    wherein at least one of the piston rods comprises a lock mechanism that blocks a return to the first compressed state during the second expanded state.

17. A piston rod mechanism according to claim 16, wherein the first and second piston rods are transferred to the second expanded state by a pressure spring.

18. A piston rod mechanism according to claim 16 wherein the first piston rod and the second piston rod are automatically transferred to the second expanded state by means of a pressure spring.

* * * * *